(12) United States Patent
Kim

(10) Patent No.: US 11,074,686 B2
(45) Date of Patent: Jul. 27, 2021

(54) SYSTEM FOR DIAGNOSING DISEASE USING NEURAL NETWORK AND METHOD THEREFOR

(71) Applicant: DEEP BIO, INC., Seoul (KR)

(72) Inventor: Sun Woo Kim, Seongnam-si (KR)

(73) Assignee: DEEP BIO, INC., Seoul (KR)

( * ) Notice: Subject to any disclaimer, the term of this patent is extended or adjusted under 35 U.S.C. 154(b) by 35 days.

(21) Appl. No.: 16/468,173

(22) PCT Filed: Dec. 6, 2017

(86) PCT No.: PCT/KR2017/014219
§ 371 (c)(1),
(2) Date: Jun. 10, 2019

(87) PCT Pub. No.: WO2018/106005
PCT Pub. Date: Jun. 14, 2018

(65) Prior Publication Data
US 2019/0385306 A1  Dec. 19, 2019

(30) Foreign Application Priority Data
Dec. 11, 2016 (KR) .................... 10-2016-0168176

(51) Int. Cl.
*G06K 9/00* (2006.01)
*G06T 7/00* (2017.01)
(Continued)

(52) U.S. Cl.
CPC ............ *G06T 7/0012* (2013.01); *G06F 17/15* (2013.01); *G06F 17/18* (2013.01); *G06N 3/0454* (2013.01);
(Continued)

(58) Field of Classification Search
CPC ........ G06T 7/0012; G06T 2207/20084; G06K 9/66; G06K 9/4628; G06K 9/32;
(Continued)

(56) References Cited

U.S. PATENT DOCUMENTS 5,638,823 A * 6/1997 Akay ................. A61B 7/00
600/528
5,769,074 A * 6/1998 Barnhill ............. G01N 33/50
600/300
(Continued)

FOREIGN PATENT DOCUMENTS

JP    2008-536211    9/2008
JP    2011-112523    6/2011
(Continued)

OTHER PUBLICATIONS

International Search Report dated Apr. 25, 2018, issued in International Application No. PCT/KR2017/014219 (with English Translation).

(Continued)

*Primary Examiner* — Amir Alavi
(74) *Attorney, Agent, or Firm* — H.C. Park & Associates, PLC

(57) ABSTRACT

A disease diagnosis system including a processor and a storage device for storing a neural network and using a biometric image and the neural network, the disease diagnosis system including a micro-neural network for receiving a first tile included in the biometric image through a first input layer, and including a plurality of first layers and an output layer, and a macro-neural network for receiving a macro-tile including the first tile and at least one or more second tiles adjacent to the first tile through a second input layer, and including a plurality of second layers and the output layer, in which the output layer includes at least one (Continued)

state channel indicating a state of a disease of a biological tissue corresponding to the first tile.

15 Claims, 12 Drawing Sheets

(51) Int. Cl.
*G16H 50/20* (2018.01)
*G06F 17/15* (2006.01)
*G06F 17/18* (2006.01)
*G06N 3/04* (2006.01)

(52) U.S. Cl.
CPC ........... *G06N 3/0472* (2013.01); *G16H 50/20* (2018.01); *G06T 2207/20084* (2013.01); *G06T 2207/30081* (2013.01)

(58) Field of Classification Search
CPC ...... G06K 9/2013; G06K 9/344; G16H 50/20; G06N 3/0454; G06N 3/0472; G06F 17/15; G06F 17/18
See application file for complete search history.

(56) References Cited

U.S. PATENT DOCUMENTS

| | | | |
|---|---|---|---|
| 5,790,761 A * | 8/1998 | Heseltine | G16H 50/20 706/16 |
| 6,004,267 A | 12/1999 | Tewari et al. | |
| 7,037,267 B1 * | 5/2006 | Lipson | A61B 8/0808 600/454 |
| 7,979,212 B2 * | 7/2011 | Gholap | G06K 9/00127 702/19 |
| 8,346,482 B2 * | 1/2013 | Fernandez | A61B 5/0002 702/19 |
| 8,798,345 B2 | 8/2014 | Sasaki et al. | |
| 9,934,364 B1 * | 4/2018 | Kumar | G01N 33/57492 |
| 10,091,426 B2 | 10/2018 | Mizutani et al. | |
| 10,109,052 B2 | 10/2018 | Chefd'hotel et al. | |
| 10,285,657 B2 * | 5/2019 | Ono | A61B 6/501 |
| 10,303,971 B2 | 5/2019 | Geva et al. | |
| 2005/0065421 A1 * | 3/2005 | Burckhardt | G06T 7/38 600/407 |
| 2008/0201282 A1 | 6/2008 | Garcia et al. | |
| 2016/0086078 A1 | 3/2016 | Ji et al. | |
| 2019/0385306 A1 * | 12/2019 | Kim | G06F 17/15 |

FOREIGN PATENT DOCUMENTS

| | | |
|---|---|---|
| JP | 2012-235796 | 12/2012 |
| JP | 2014-049118 | 3/2014 |
| KR | 10-1563569 | 10/2015 |
| KR | 10-2016-0034814 | 3/2016 |
| WO | 2015177268 | 11/2015 |
| WO | 2016189605 | 12/2016 |
| WO | 2016193979 | 12/2016 |

OTHER PUBLICATIONS

Extended European Search Report dated Jun. 9, 2020, issued for EP 17879144.8.
A prostate cancer computer-aided diagnosis system using multimodal magnetic resonance imaging and targeted biopsy labels, Liu et al., SPIE-International Society for Optical Engineering, vol. 8670, Feb. 26, 2013, p. 86701G.

* cited by examiner

SYSTEM FOR DIAGNOSING DISEASE USING NEURAL NETWORK AND METHOD THEREFOR

CROSS REFERENCE TO RELATED APPLICATIONS

This application is a National Stage Entry of International Patent Application No. PCT/KR2017/014219, filed on Dec. 6, 2017, and claims priority from and the benefit of Korean Patent Application No. 10-2016-0168176, filed on Dec. 11, 2016, each of which is incorporated by reference for all purposes as if fully set forth herein.

BACKGROUND

Field

Exemplary embodiments relate to a disease diagnosis system using a neural network and a method thereof, and more specifically, to a system capable of diagnosing a predetermined disease (e.g., prostate cancer) from an image of a biological tissue using a well-trained neural network and a method thereof.

Discussion of the Background

One of the important tasks performed by a pathology department is performing a diagnosis for determining a state or a symptom of a specific disease by reading a biometric image of a patient. Such a diagnosis method relies on the experience and knowledge of medical workers trained for an extended period of time.

Recently, attempts for automating a work, such as recognizing or classifying an image using a computer system, are actively being made with the development of machine learning. More particularly, attempts are made to automate diagnosis that would normally be performed by skilled medical workers using a neural network (e.g., a deep learning method using a convolution neural network (CNN)), which is a type of machine learning.

Since the diagnosis through deep learning using a neural network, such as CNN, is not simply automating the experience and knowledge of skilled medical workers, but rather finding out distinctive factors and deriving a desired answer through self-learning, there are occasions when several features of a disease factor unknown to the skilled medical workers are found in an image.

Generally, diagnosis of a disease through a neural network using a biomedical image uses a segment of the biomedical image, i.e., a tile. For example, a skilled medical worker annotates a state of a specific disease (e.g., whether a cancer has been manifested) to a corresponding tile, and the neural network is trained using a plurality of annotated tiles as training data. At this point, a convolution neural network may be used as the neural network.

In this case, the conventionally trained neural network may determine a state of a disease of a corresponding tile using only the image features of the tile. However, in general, determining a state of a specific biological tissue for a specific disease may also require a consideration of states (e.g., a shape, whether a specific pattern exists and the like) of the tissues surrounding the specific biological tissue, as well as the specific biological tissue itself.

SUMMARY

A neural network according to an exemplary embodiment and a method of the same may provide a diagnosis system capable of enhancing accuracy by using neighboring tiles, as well as a specific tile, for learning to determine the states (e.g., whether a disease has been manifested, an index indicating a state of a disease, and the like) of a disease of the specific tile.

A neural network according to an exemplary embodiment and a method of the same may also provide a diagnosis system capable of outputting information on a factor working as the basis for determining a state of a disease of a tile, rather than simply outputting information on the state.

Additional features of the inventive concepts will be set forth in the description which follows, and in part will be apparent from the description, or may be learned by practice of the inventive concepts.

A disease diagnosis system implemented in a system including a processor and a storage device for storing a neural network and using a biometric image and the neural network according to an exemplary embodiment includes a micro-neural network for receiving a first tile included in the biometric image through a first input layer, the micro-neural network including a plurality of first layers and an output layer, and a macro-neural network for receiving a macro-tile including the first tile and at least one or more second tiles adjacent to the first tile through a second input layer, the macro-neural network including a plurality of second layers and the output layer, in which the output layer includes at least one state channel indicating a state of a disease of a biological tissue corresponding to the first tile.

The output layer may be determined on the basis of output data of a first right-before layer included in the first layers and located closest to the output layer, and a second right-before layer included in the second layers and located closest to the output layer.

The macro-neural network may have a larger stride than the micro-neural network.

The output layer may include the state channel and at least one correlation factor channel indicating a degree of manifestation of a correlation factor associated with a value of the state channel.

The disease may be prostate cancer.

The state channel may indicate a probability of a biomedical tissue corresponding to the first tile to have a Gleason pattern value of a predetermined range.

The correlation factor channel may include a first channel indicating a probability that a cell nucleus of the biological tissue corresponding to the first tile satisfies a predetermined condition, a second channel indicating a probability that the biological tissue corresponding to the first tile is classified as a single cell layer, a third channel indicating a probability that the biological tissue corresponding to the tile is classified as a high density gland, and a fourth channel indicating a probability that the biological tissue corresponding to the first tile is classified as normal stroma.

A disease diagnosis system implemented in a system including a processor and a storage device for storing a neural network and using a biometric image and the neural network according to another exemplary embodiment includes an input layer for receiving a first tile included in the biometric image, a plurality of layers, and an output layer including at least one state channel indicating a state of a disease of a biological tissue corresponding to the first tile, and at least one correlation factor channel indicating a degree of manifestation of a correlation factor associated with a value of the state channel.

A method of diagnosing a disease using a neural network, performed by a disease diagnosis system implemented in a system including a processor and a storage device and using a biometric image and the neural network according to another exemplary embodiment includes the steps of: storing a micro-neural network for receiving a first tile included in the biometric image through a first input layer and including a plurality of first layers and an output layer, and a macro-neural network for receiving a macro-tile including the first tile and at least one or more of second tiles adjacent to the first tile through an input layer and including a plurality of second layers and the output layer; and training the micro-neural network and the macro-neural network using annotation information annotated in the first tile to correspond to the output layer, in which the output layer includes at least one state channel indicating a state of a disease of a biological tissue corresponding to the first tile.

The method may further include the steps of: receiving a target tile included in a diagnosis target biometric image, by the neural network including the trained micro-neural network and macro-neural network; and outputting an output data corresponding to the output layer through the neural network.

The output layer may be determined on the basis of output data of a first right-before layer included in the first layers and located closest to the output layer and a second right-before layer included in the second layers and located closest to the output layer.

A method of diagnosing a disease using a neural network, performed by a disease diagnosis system implemented in a system including a processor and a storage device for storing the neural network and using a biometric image and the neural network according to another exemplary embodiment includes the steps of: storing the neural network including a first input layer for receiving a first tile included in the biometric image, a plurality of layers, and an output layer; and training the neural network using the first tile and annotation information of the first tile corresponding the output layer, in which the output layer includes at least one state channel indicating a state of a disease of a biological tissue corresponding to the first tile, and at least one correlation factor channel indicating a degree of manifestation of a correlation factor associated with a value of the state channel.

The method may be implemented through a computer program installed in a data processing device and recorded in a medium.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
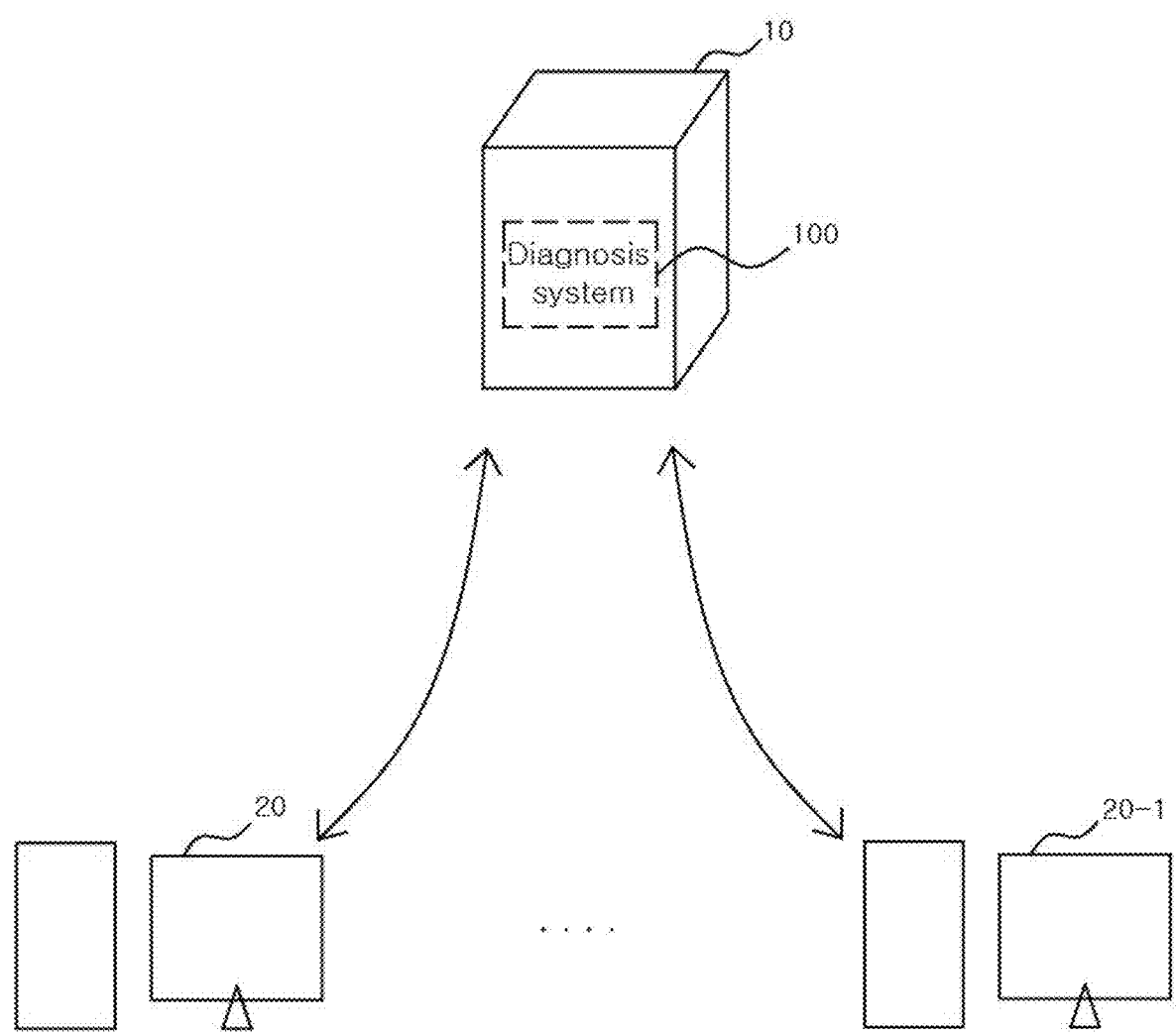
FIG. 1 is a schematic view of a disease diagnosis system using a neural network according to an exemplary embodiment.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As is customary in the field, some exemplary embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some exemplary embodiments may be physically separated into two or more interacting and discrete blocks, units, and/or modules without departing from the scope of the inventive concepts. Further, the blocks, units, and/or modules of some exemplary embodiments may be physically combined into more complex blocks, units, and/or modules without departing from the scope of the inventive concepts.

FIG. 1 is a schematic view of a disease diagnosis system using a neural network according to an exemplary embodiment.

Referring to FIG. 1, a disease diagnosis system 100 using a neural network according to an exemplary embodiment may be installed in a predetermined server 10. As used herein, the server 10 may refer to a data processing device having computing capability for implementing various features described herein, such as a personal computer, a portable terminal, or any data processing device that can be accessed by a client through a network, without being limited thereto.

Figure 3:
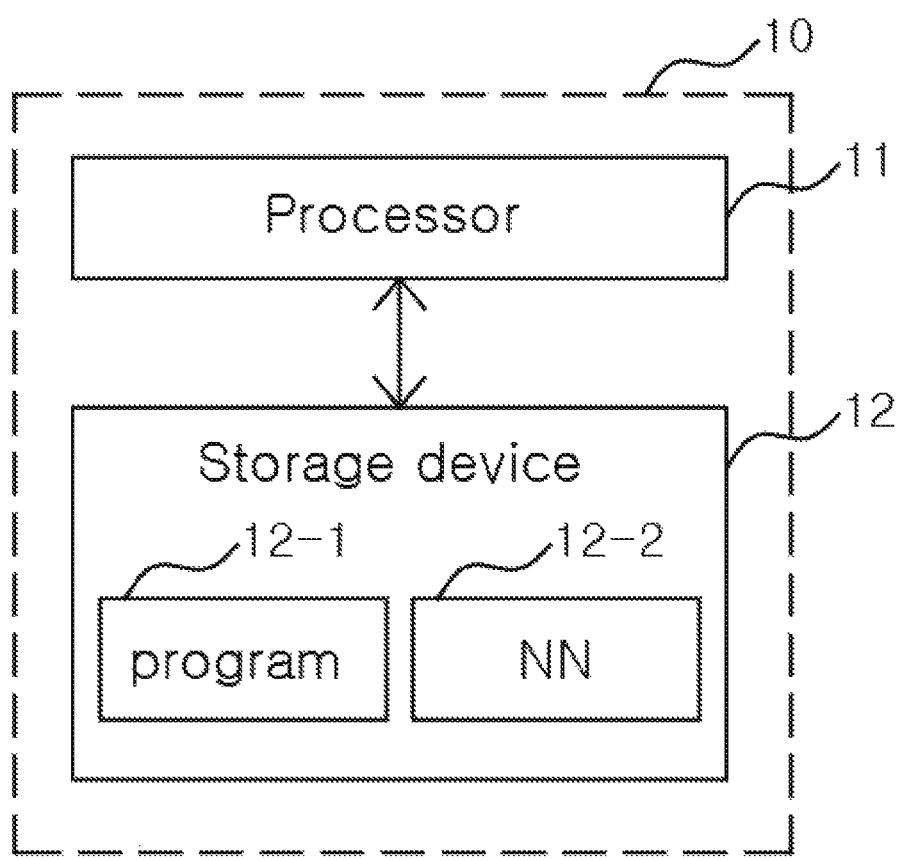
FIG. 3 is a schematic view of a disease diagnosis system using a neural network according to an exemplary embodiment.

The server 10 may include a processor 11 and a storage device 12 as shown in FIG. 3. As used herein, the processor 11 may refer to a computing device which can drive a program 12-1 for implementing various features described herein, and the processor 11 may perform diagnosis using the program 12-1 and a neural network (NN) 12-2.

As used herein, the storage device 12 may refer to a data storage which can store the program 12-1 and the neural network 12-2, and may be implemented as a plurality of storage depending on applications. In addition, the storage device 10 may also refer to a temporary storage device, a memory or the like, which can be included in the processor 11, as well as a main memory device included in the server 10.

Although the diagnosis system 100 is illustrated as a physical device in FIG. 1 or 3, in some exemplary embodiments, a plurality of physical devices may be organically combined to implement the diagnosis system 100.

As used herein, the diagnosis system 100 performing a diagnosis may refer that a series of processes, such as receiving a biometric image showing a biological tissue and outputting an output data, may be performed. The output data may be information outputted from an output layer of a neural network used by the diagnosis system 100, and the output data may include state information showing a state of a specific disease of a biological tissue corresponding to a tile included in the biometric image. The state information may be information outputted from a state channel included in the output layer.

For example, the state information may be probability information on whether a specific disease (e.g., a specific type of cancer) is manifested in a tissue corresponding to the tile. In some exemplary embodiments, the state information may be information indicating a degree of progression of a specific disease (or a probability of being corresponding to the degree of progression), in addition to indicating whether the specific disease is manifested. For example, when the diagnosis system 100 performs a diagnosis of prostate cancer to be described below, a Gleason pattern or a Gleason score, which are indices for indicating a degree of progression of prostate cancer, may be included in the state information. The Gleason pattern has a value between 2 and 5, and the larger value indicates a higher the degree of the manifested prostate cancer. Accordingly, the state information may include a probability that a biological tissue corresponding to a tile, which is a target of diagnosis, corresponds to a specific value (e.g., 3, 4 or 5) of the Gleason pattern.

The state information may be in plural. For example, first state information may indicate a probability of the Gleason pattern for being 3, second state information may indicate a probability of the Gleason pattern for being 4, and third state information may indicate a probability of the Gleason pattern for being 5. All the state channels corresponding to the first state information, the second state information, and the third state information may be defined in the output layer. According to an exemplary embodiment, state information indicating that the Gleason pattern has a probability of a predetermined range (e.g., 3 to 5, 4 to 5 or the like) may be defined. More particularly, a piece of state information may correspond to a plurality of indices indicating a progression state of a disease.

In this manner, the state channel included in the output layer may be determined according to how a corresponding tile is annotated for learning.

According to an exemplary embodiment, correlation factor channels and the state channels may be included in the output layer. More particularly, when the diagnosis system 100 is implemented to be included in a predetermined server 10, the diagnosis system 100 may perform communication with at least one client (e.g., 20 or 20-1) which can access the server 10. In this case, the client (e.g., 20 or 20-1) may transmit a biometric image to the diagnosis system 100, and the diagnosis system 100 may perform diagnosis on the transmitted biometric image. In addition, the diagnosis system 100 may transmit a diagnosis result to the client (e.g., 20 or 20-1).

The diagnosis system 100 may perform diagnosis using a neural network according to an exemplary embodiment. In this case, the diagnosis system 100 may first perform a process for training the neural network to perform the diagnosis.

Accordingly, the diagnosis system 100 may be a system that receives a trained neural network and a program for performing diagnosis using the neural network from the outside and performs the diagnosis, or a system that additionally performs the training of the neural network. In some exemplary embodiments, the diagnosis system 100 may be implemented as a dedicated device rather than a general-purpose data processing device, and in this case, a separate device for scanning the biometric image may be further provided.

The neural network used by the diagnosis system 100 according to an exemplary embodiment may include a micro-neural network and a macro-neural network.

The micro-neural network may refer to a network which performs a series of processes for performing training using a specific tile and performing diagnosis on the tile using image features of the tile itself.

The macro-neural network may refer to a network which performs a series of processes for performing training using the tile, a macro-tile including the tile, and at least one of adjacent tiles, and performing diagnosis on the tile using image features of the entire macro-tile.

Accordingly, the neural network according to an exemplary embodiment may have characteristics of performing diagnosis on a specific tile, by additionally considering an image of at least one of adjacent tiles to perform diagnosis on the specific tile. By considering not only a biological tissue actually corresponding to a specific tile, but also the states of tissues around the biological tissue for diagnosis of the biological tissue, the accuracy on the diagnosis of a disease may be improved. In addition, when a biometric image is divided into a plurality of tiles, such may have a strong effect on the influence of a diagnosis result, which can be generated according to the method of dividing the tiles or the position of a biological tissue corresponding to a divided area.

Figure 2:
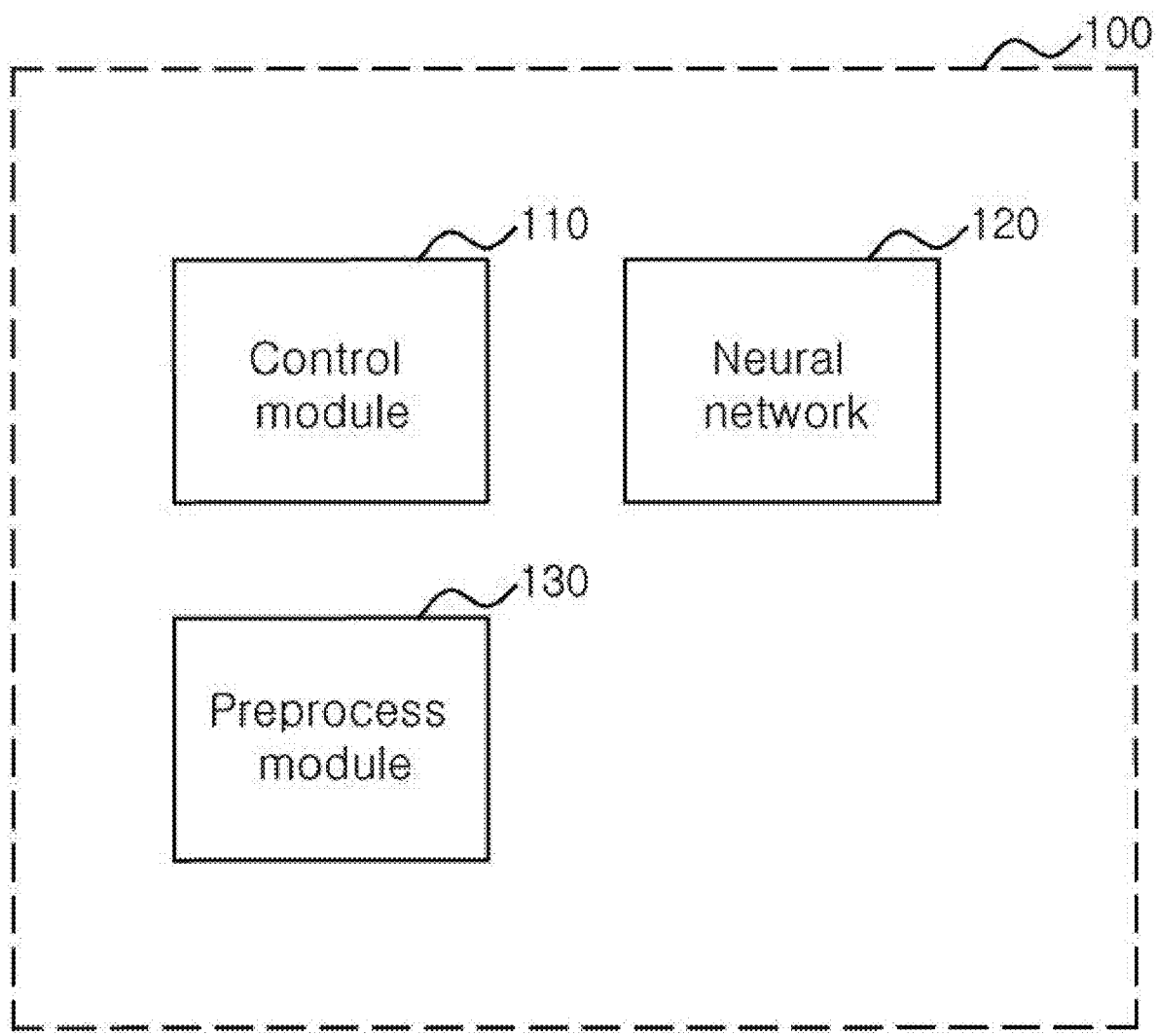
FIG. 2 is a diagram schematically illustrating a logical configuration of a disease diagnosis system using a neural network according to an exemplary embodiment.

A diagnosis system 100 according to an exemplary embodiment may have the configuration shown in FIG. 2.

FIG. 2 is a diagram schematically illustrating a logical configuration of a disease diagnosis system using a neural network according to an exemplary embodiment.

Referring to FIG. 2, the diagnosis system 100 includes a control module 110 and a neural network module 120, in which a neural network is stored. In addition, the diagnosis system 100 may further include a preprocess module 130.

The diagnosis system 100 may have a logical configuration provided with hardware resources and/or software needed for implementing the spirit of the present invention, and is not limited to a particular physical configuration component or a device. For example, the diagnosis system 100 may be a logical combination of hardware and/or software provided to implement the spirit of the present invention, and if needed, the diagnosis system 100 may be installed in multiple devices separated from each other, and separately perform its function to be implemented as a set of logical configurations for implementing the spirit of the invention. In addition, the diagnosis system 100 may also be a set of configurations separately implemented for each function or role for implementing the spirit of the present invention. For example, the control module 110, the neural network module 120, and/or the preprocess module 130 may be located in different physical devices or in the same physical device. In addition, in some exemplary embodiments, combinations of software and/or hardware configuring the control module 110, the neural network module 120, and/or the preprocess module 130 may also be located in different physical devices, and each of the modules may be implemented as the configurations located in the different physical devices are organically combined with each other.

As used herein, a module may refer to a functional or structural combination of hardware for performing the spirit of the invention and software for driving the hardware. For example, the module may be a logical unit of a predetermined code and hardware resources for performing the predetermined code, and thus, the module may not be limited to physically connected codes or a kind of hardware.

The control module 110 may control other configurations (e.g., the neural network module 120 and/or the preprocess module 130) included in the diagnosis system 100 to implement the spirit of the invention.

In addition, the control module 110 may perform diagnosis by using the neural network stored in the neural network module 120. In some exemplary embodiments, performing a diagnosis may include outputting a channel value of at least one channel defined in the output layer as described above. Each channel value may indicate the probability that a tile, which is a target of diagnosis, corresponds to the information defined by the corresponding channel.

The neural network module 120 may store a neural network. The neural network may be a set of information expressing a series of design considerations defining the neural network. According to an exemplary embodiment, the neural network may be a convolution neural network.

The convolution neural network may include an input layer, a plurality of hidden layers, and an output layer, as well known in the art. Each of the plurality of hidden layers may include a convolution layer and a pooling layer (or a sub-sampling layer).

The convolution neural network may be defined by a function defining each of the layers, a filter, a stride, a weight factor and so on. In addition, the output layer may be defined as a fully connected feed-forward layer.

Design considerations of each layer configuring the convolution neural network are well-known in the art. For example, known functions may be used for the number of layers to be included in a plurality of layers, a convolution function for defining the plurality of layers, a pooling function, and an activation function, or functions separately defined to implement the spirit of the present invention may be used.

For example, the convolution function may include a discrete convolution sum or the like. Max pooling, average pooling or the like may be exemplarily used as the pooling function. In some exemplary embodiments, the activation function may be a sigmoid function, a tangent hyperbolic (tanh) function, a rectified linear unit (ReLU) and the like.

When design considerations of the convolution neural network are defined, the convolution neural network, for which the design considerations are defined, may be stored in the storage unit. In addition, if the convolution neural network is trained, a weight factor corresponding to each layer may be specified, and stored in the storage unit.

Training of the convolution neural network may include a process of determining weight factors of the layers. In addition, if the convolution neural network is trained, the trained convolution neural network may receive an input data through the input layer, and output an output data through a predetermined output layer.

The neural network according to an exemplary embodiment may be defined by selecting any one or more of widely-known design considerations as described above, or independent design considerations may be defined for the neural network.

The control module 110 may input an input data into the neural network stored in the neural network module 120, e.g., the trained neural network. In addition, the control module 110 may output an output data by performing computations defined by the neural network.

The preprocess module 130 may perform preprocess on a biometric image before performing diagnosis using the neural network. For example, preprocess of the biometric image may include a process of tiling the biometric image into tiles of a predefined size, and other necessary processes for a proper image processing.

As described above, a neural network according to an exemplary embodiment has characteristics of including a micro-neural network and a macro-neural network as described above, which will be described in more detail below with reference to FIG. 4.

Figure 4:
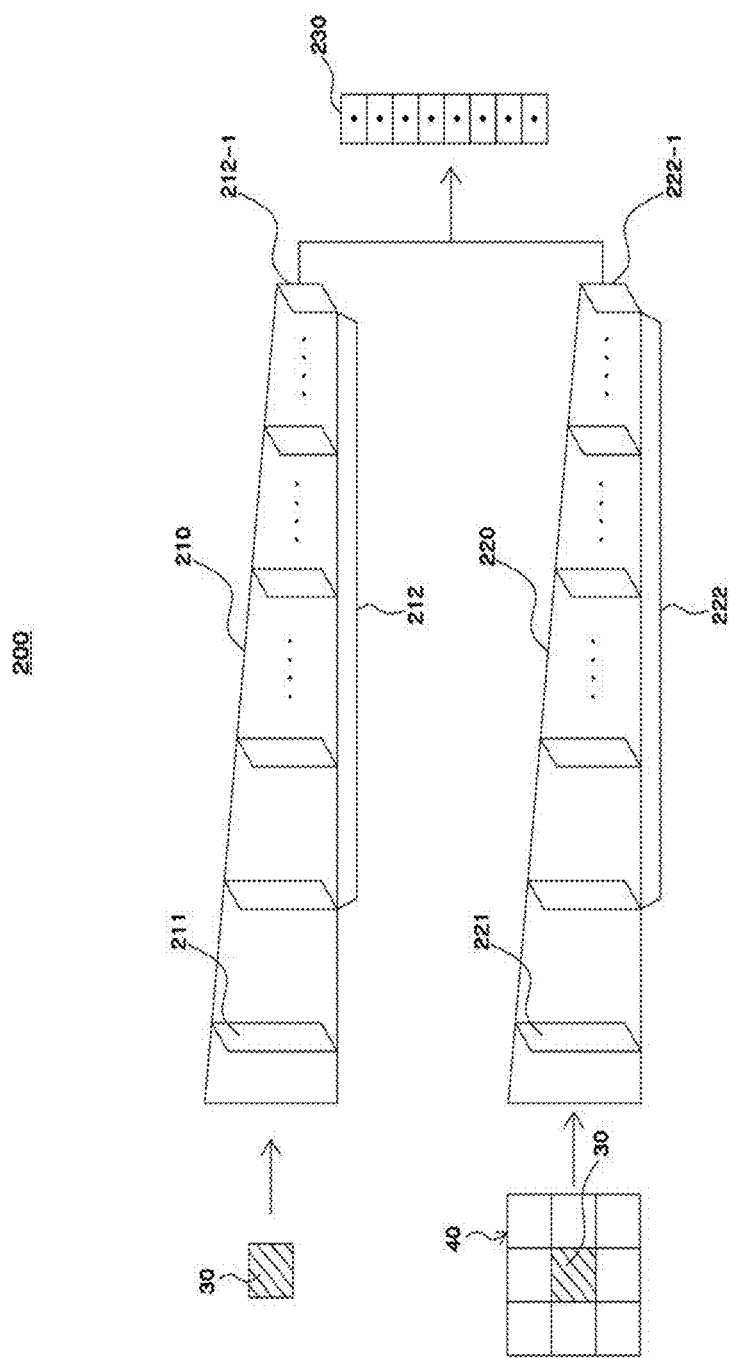
FIG. 4 is a schematic view of a neural network according to an exemplary embodiment.

FIG. 4 is a schematic view of a neural network according to an exemplary embodiment.

Referring to FIG. 4, a neural network 200 according an exemplary embodiment includes a micro-neural network and a macro-neural network.

The micro-neural network includes a plurality of layers 210 and an output layer 230. The layers 210 include an input layer 211 and a plurality of hidden layers 212.

The macro-neural network includes a plurality of layers 220 and the output layer 230. The layers 220 include an input layer 221 and a plurality of hidden layers 222.

The micro-neural network may receive a specific tile 30, and output a diagnosis result of the specific tile 30, such as output data defined in the output layer 230.

In addition, the macro-neural network may receive a macro-tile 40 including the specific tile 30 and at least one of adjacent tiles to the specific tile 30, and output a diagnosis result of the specific tile 30.

The neural network 200 according to the illustrated exemplary embodiment may output a diagnosis result that is based on image features of the adjacent tiles to the specific tile 30, as well as image features of the specific tile 30, to output a diagnosis result of the specific tile 30.

Although FIG. 4 exemplarily illustrates a case where tiles surrounding a tile are used as the macro-tile 40, the inventive concepts are not limited thereto, and various other cases may be applicable.

The output layer 230 may receive output data of a first right-before layer 212-1, which is a layer included in the micro-neural network right before (or closest to) the output layer 230, and output data of a second right-before layer 222-1, which is a layer included in the macro-neural network right before (or closest to) the output layer 230, and output an output data defined in the output layer 230. The first right-before layer 212-1, the second right-before layer 222-1, and the output layer 230 may be fully connected.

Any one of various functions, which outputs an input data received through the input layer to the output layer 230 as an output data through the neural network 200 as a result, may be used as a feed-forward function which defines the output layer 230.

In this manner, the neural network 200 is trained to output an output data of the output layer 230 corresponding to annotation values of a plurality of training data, considering image features of the specific tile 30 and image features of the macro-tile 40 including the specific tile 30, to perform diagnosis on the specific tile 30.

More particularly, a plurality of training data is used to train the neural network 200, and the plurality of training data may include a specific tile 30 and a macro-tile 40 in pairs. In addition, the macro-tile 40 may also perform training using annotation information of the specific tile 30.

Then, the neural network 200 may be trained to output an output data corresponding to the annotation information of the specific tile 30, considering the image features of the specific tile 30 and the macro-tile 40.

In addition, when the trained neural network 200 receives a target tile, which may be a target of diagnosis, and a macro-tile corresponding to the target tile as input data of the input layers of the micro neural network and the macro-neural network, the neural network 200 may output a diagnosis result of the target tile, such as an output data of the output layer 230.

Meanwhile, the macro-neural network may have a larger stride as compared to the micro-neural network. This may mean that the macro-neural network intermittently extracts image features included in the macro-tile 40 as compared to the micro-neural network. This may also mean that since the macro-neural network diagnoses the specific tile 30, the macro-neural network may not need to extract image features very densely and go through a process of abstracting the extracted image features like the micro-neural network. Such may also limit the image features of adjacent tiles having a greater effect than that by the specific tile 30, on the diagnosis of the specific tile 30. Accordingly, a network can be designed more efficiently by setting a stride value of the macro-neural network to be larger than that of the micro-neural network. According to an exemplary embodiment, the stride value used in the micro-neural network may be 1, and a value of 2 or 3 may be used as the stride value in the macro-neural network.

In addition, a larger stride value may not need to be commonly applied to all hidden layers, and a stride value applied only to some convolution layers of early stage may be larger in the macro-neural network than in the micro-neural network.

Meanwhile, the output layer 230 may output a diagnosis result of the specific tile 30, which is a target of diagnosis, as an output data. The diagnosis result may include at least information on the state of a disease of the specific tile 30. Information on the state of a disease may be information on whether a specific disease is manifested (or a probability value) in the specific tile 30.

However, according to an exemplary embodiment, information indicating a degree of progression of a disease in further detail may be included in the information on the state of a disease according to disease type. Hereinafter, type of a disease diagnosed by the diagnosis system 100 will be described as prostate cancer, however, the inventive concepts are not limited a particular disease.

Figure 5:
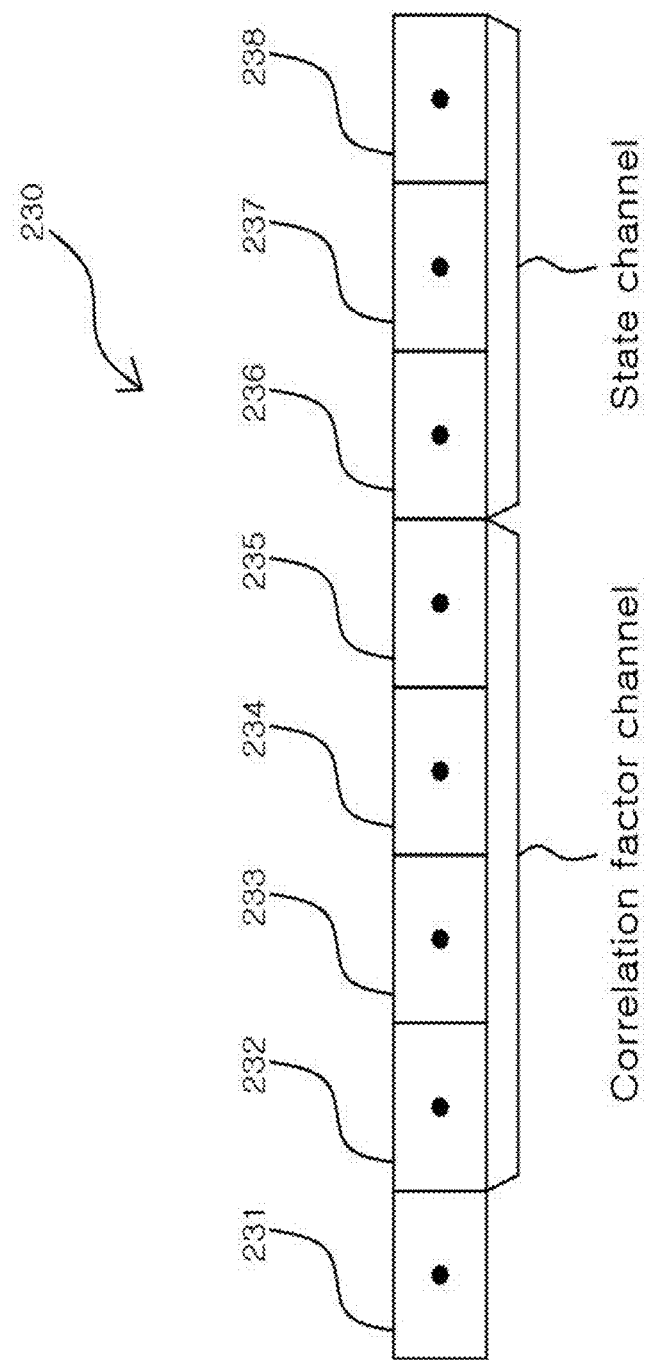
FIG. 5 is a schematic view of an output layer of a neural network according to an exemplary embodiment.

FIG. 5 is a schematic view of an output layer of a neural network according to an exemplary embodiment.

Referring to FIG. 5, an output layer 230 according to an exemplary embodiment may include at least one channel 231 to 238.

The output layer 230 may include at least a state channel (e.g., 236, 237 or 238) indicating information on the state of a disease as described above. The state channels (e.g., 236, 237 and 238) may be information indicating a degree of progression of a disease, respectively. For example, a first state channel 236 may be information indicating a probability of having a first value (e.g., Gleason pattern of 3), which may be any values among Gleason pattern, e.g., an index indicating a degree of progression of prostate cancer. A second state channel 237 and a third state channel 238 may be information indicating probabilities having a second value (e.g., Gleason pattern of 4) and a third value (e.g., Gleason pattern of 5), which are different values among the values of Gleason pattern. In this manner, when an index indicating a degree of progression is defined according to the type of a disease, a degree of progression of a corresponding disease may be further diagnosed, in addition to the manifest of a disease.

Meanwhile, according to an exemplary embodiment, at least one of correlation factor channels (e.g., 232, 233, 234, and 235) indicating a degree of manifestation of a correlation factor associated with a value of the state channel, as well as information on whether a disease is manifested in a tile, which is a target of diagnosis, or how much a disease has progressed, may be further included in the output layer 230.

More particularly, the correlation factor channels (e.g., 232, 233, 234, and 235) may be information indicating whether individual factors, which are the basis for determining whether a disease is manifested or a degree of progression of the disease, are manifested. For example, manifestation of prostate cancer or a degree of progression thereof may be determined by considering one or more individual factors, such as whether the state of a cell nucleus satisfies a predetermined condition, whether the gland cell wall is made up of a single layer, whether the gland is concentrated more than a predetermined level, and/or whether the shape of stroma is normal.

In particular, a channel value of the channel state is determined by combination of individual factors, and according to an exemplary embodiment, the individual factors may be defined as separate channels, and whether the individual factors are manifested is also diagnosed through the training.

In this manner, when the correlation factor channels (e.g., 232, 233, 234 and 235) are defined in the output layer 230, the problem from when only the state channel exists, such as a medical staff not knowing how the output value of the corresponding state channel has been derived, may be solved. More particularly, according to an exemplary embodiment, the diagnosis system 100 may additionally provide an output value of the state channel, e.g., output values of the correlation factor channels (e.g., 232, 233, 234 and 235), which may provide information in regards to whether individual factors that form a basis for determining manifestation of a disease or its progress thereof have been manifested. As such, the diagnosis system 100 may further increase reliability of the diagnosis result. In addition, since it can be easily confirmed whether the output value of the correlation factor channel (e.g., 232, 233, 234, and 235) and the output value of the state channel match each other, the status of the progress of the training of the diagnosis system 100 can be easily determined, and thus, may provide an effective training for the neural network 200 itself. Furthermore, it has been confirmed that the neural network 200 has a more accurate diagnosis rate when the correlation factor channels (e.g., 232, 233, 234, and 235) are separately trained. This may mean that by including the correlation factor channels (e.g., 232, 233, 234, and 235) in the output layer 230, the neural network 200 considers individual factors in determining the output value of the status channel.

When the diagnosis system 100 is trained for diagnosis of prostate cancer, the correlation factor channel may include a channel indicating a probability that the cell nucleus of a biological tissue corresponding to the tile satisfies a specific condition. For example, the specific condition may include conditions, such as a case of a relatively large nucleus, a case of a dark color, a case of a clearly visible nucleolus, a degree close to the original shape of a nucleus, and the like, and the more these conditions are satisfied, the higher the probability that prostate cancer has been developed or a degree of progression thereof is severe.

In addition, the correlation factor channels (e.g., 232, 233, 234 and 235) may include a channel indicating a probability that a biological tissue corresponding to the tile is classified as a single cell layer, i.e., classified as a case of clearly showing a gland cell wall as a single layer. When the characteristics of a single cell layer are manifested, it is highly probable that prostate cancer has been developed or a degree of progression thereof is severe.

In addition, the correlation factor channels (e.g., 232, 233, 234, and 235) may include a channel indicating a probability that a biological tissue corresponding to the tile is classified as a high density gland. For example, when more than a predetermined number of glands are concentrated within a predetermined range, it may be determined that the probability of developing prostate cancer is high or a degree of progression thereof is severe.

In addition, the correlation factor channels (e.g., 232, 233, 234, and 235) may include a channel indicating a probability that a biological tissue corresponding to the tile is classified as normal stroma. More particularly, the probability of prostate cancer or the degree of progression may be low when the biological tissue has a shape of normal stroma.

In order for the trained neural network 200 to output each of the channel values defined in the output layer 230 as an output data, annotation values of the channels corresponding to the output layer 230 should be annotated to the training data, e.g., the tile and the macro-tile. In this case, a professional who is capable of annotating the channel values may be required.

In an exemplary embodiment, a predetermined channel (e.g., 231) among the channels included in the output layer 230 may not include meaningful information. More particularly, a corresponding channel may be a channel that is not used for learning and diagnosing. This is because the output layer 230 may be designed to include at least one unused channel if it is advantageous for the output layer 230 to have as many channels as a multiple of two when a network is designed.

As such, to diagnose any one tile, which is a target of diagnosis, the neural network 200 used by the diagnosis system 100 according to an exemplary embodiment may have characteristics of performing diagnosis with further higher accuracy by considering an image of a macro-tile including the tile, as well as the tile itself.

In addition, since the neural network 200 includes at least a correlation factor channel, in addition to outputting a state channel as an output data, the reliability of a diagnosis result can be secured, and it is effective for learning of the neural network 200. As the correlation factor channels are included in the output layer, the accuracy of the diagnosis result itself of the state channel may be improved.

Figure 6:
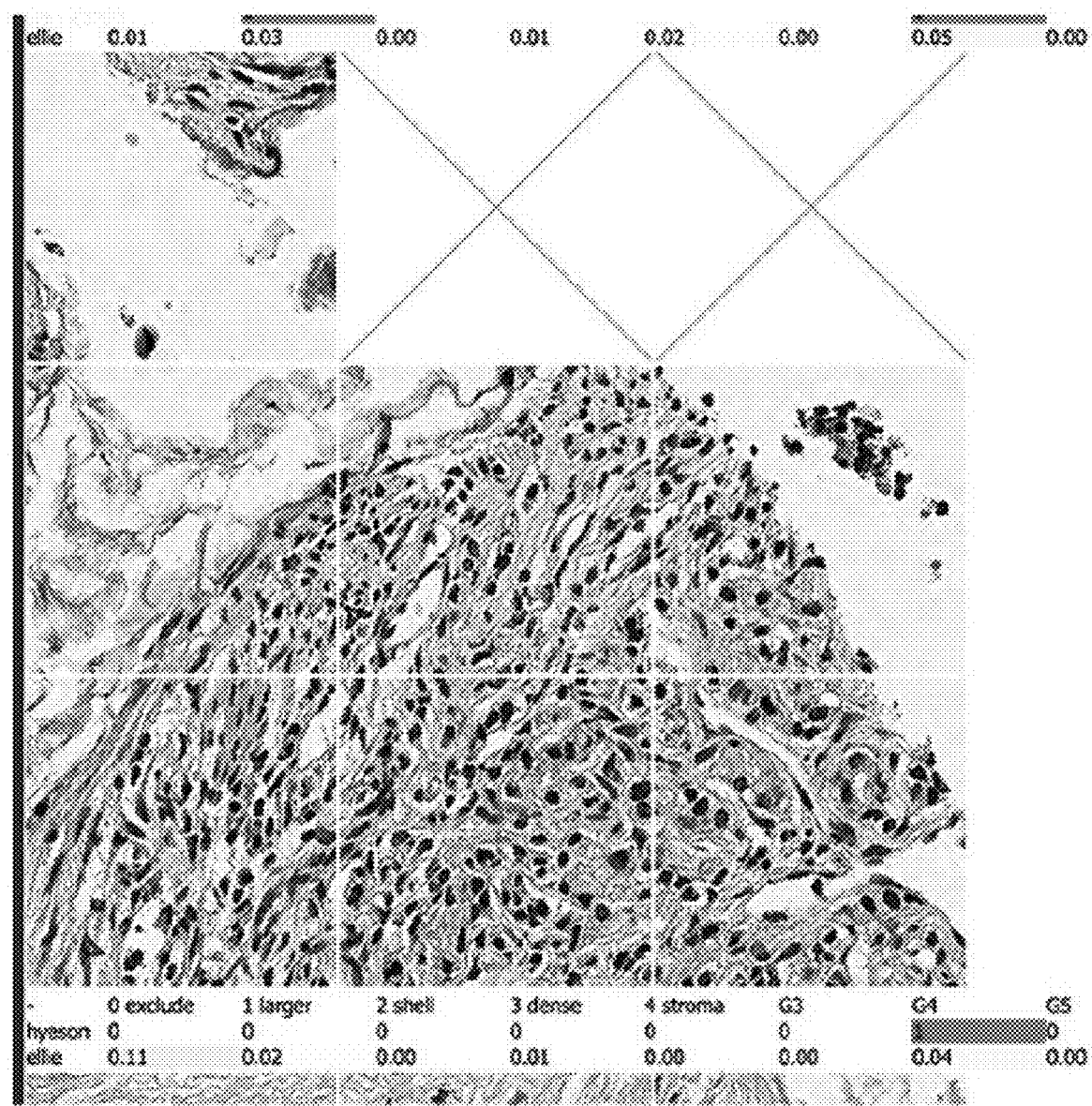
FIG. 6 is a view exemplarily illustrating annotation information for training a neural network according to an exemplary embodiment.

FIG. 6 is a view exemplarily illustrating annotation information for training a neural network according to an exemplary embodiment.

Referring to FIG. 6, annotation information of a macrotile as shown in FIG. 6 may be needed to train the neural network 200 according to an exemplary embodiment. In FIG. 6, values of the channels defined in the output layer 230 are annotated for the tile existing at the center of the macro-tile. For example, eight channel values are annotated in the lower portion of the image shown in FIG. 6. More particularly, A first channel is an unused channel, a second channel is a correlation factor channel for a cell nucleus as described above, a third channel is a correlation factor channel related to a single cell layer, a fourth channel is a correlation factor channel for a high density gland, a fifth channel is a correlation factor channel for whether stroma is a normal, a sixth channel is a state channel in which the Gleason pattern has a value of 3, a seventh channel is a state channel in which the Gleason pattern has a value of 4, and an eighth channel is a state channel in which the Gleason pattern has a value of 5. In addition, it has been annotated that the Gleason pattern has a state of 4 for the tile located at the center of the macro-tile. Although not shown in FIG. 6, annotation may be further performed on a correlation factor channel, which is the basis for determining that the Gleason pattern is 4.

The neural network 200 may be trained as the annotated information, the annotated tile, and the macro-tile including the tile are used as training data.

FIGS. 7 to 10 are views illustrating correlation factors in a neural network according to an exemplary embodiment.

Figure 7:
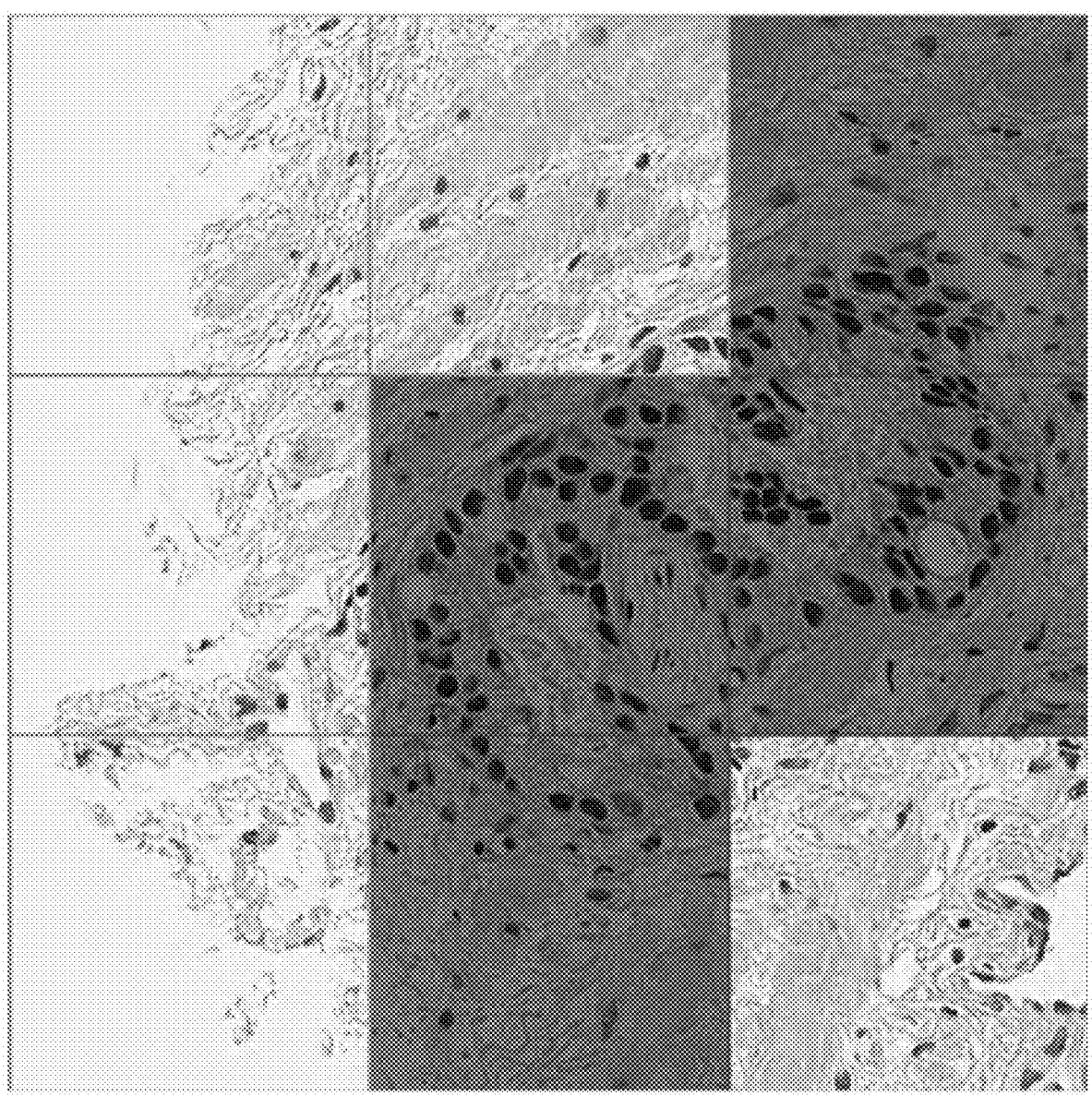
FIGS. 7, 8, 9, and 10 are views illustrating correlation factors in a neural network according to an exemplary embodiment.
Figure 8:
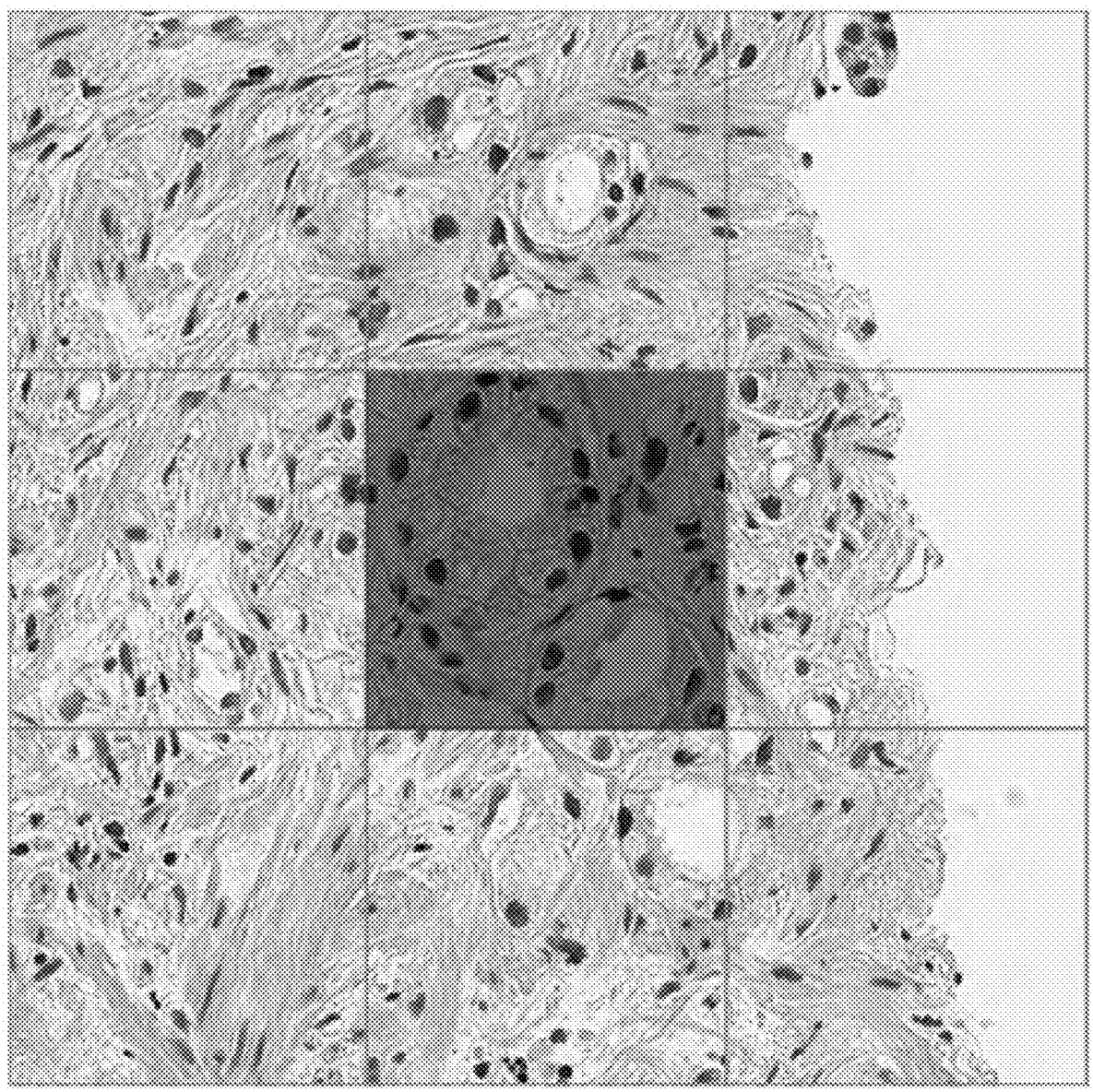
Figure 9:
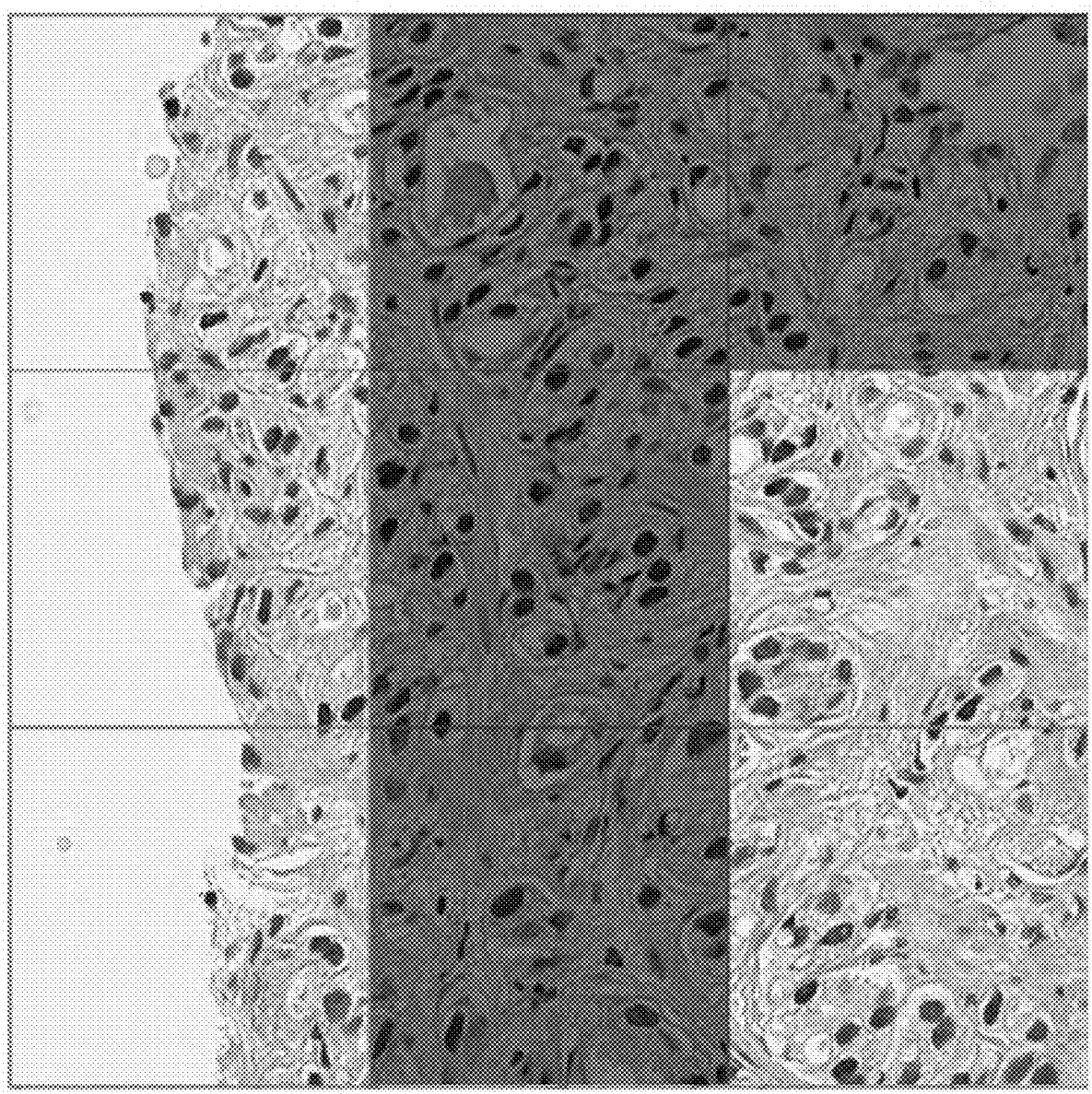
Figure 10:
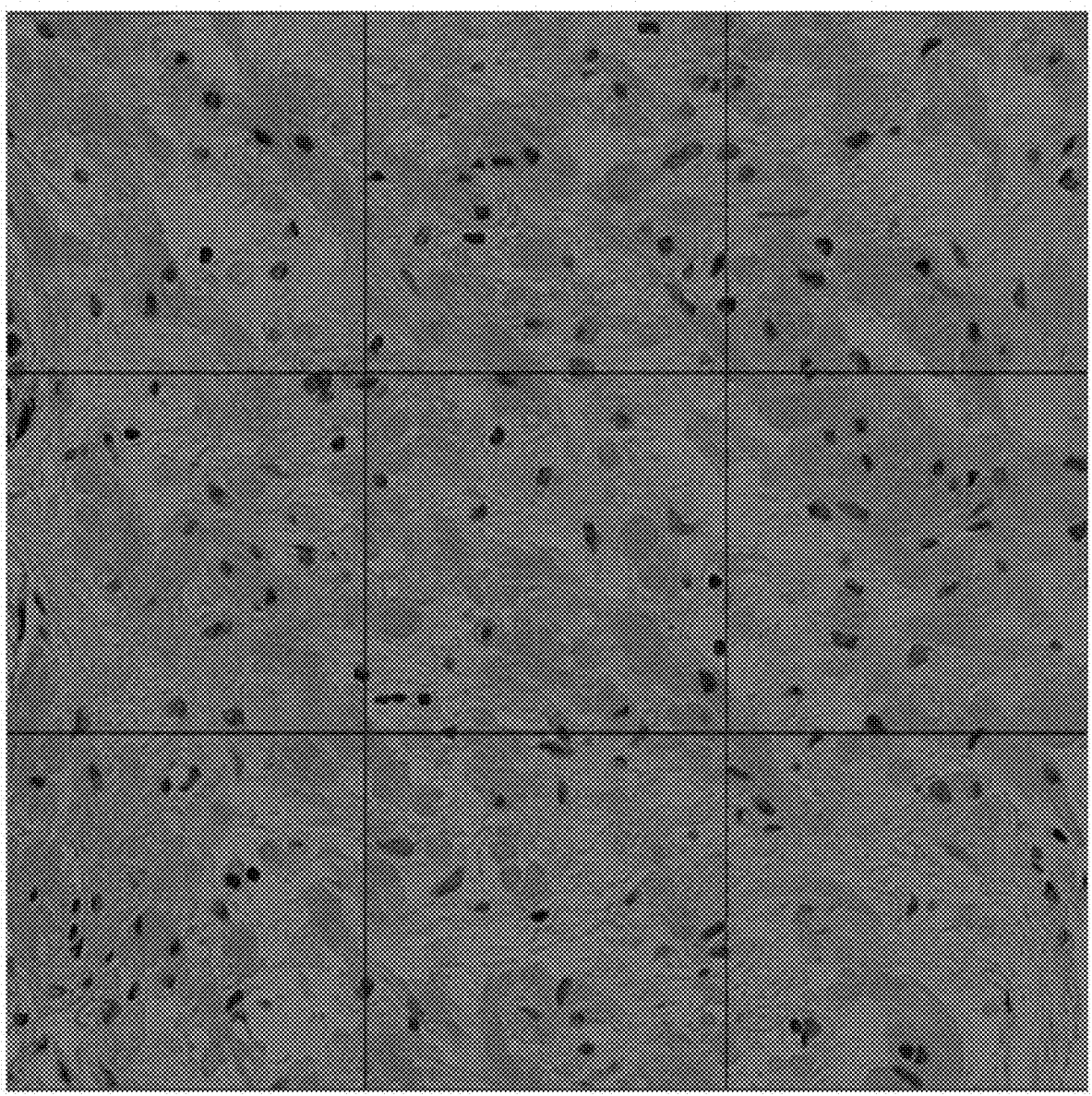

FIGS. 7 to 10 show exemplary tiles, in which a corresponding value is annotated (or diagnosed) to a correlation factor channel as described above. FIG. 7 shows inverted views of tiles satisfying conditions on the cell nucleus among the tiles, FIG. 8 shows inverted views of tiles corresponding to a single cell layer, FIG. 9 shows inverted views of tiles corresponding to a high density gland, and FIG. 10 shows inverted views of tiles corresponding to normal stroma.

Accordingly, the diagnose system 100 according to an exemplary embodiment may extract tiles, in which a specific disease is manifested or that correspond to a specific state of progression, from a biometric image including a plurality of tiles, and may separately extract tiles in which specific individual factors are manifested.

Figure 11:
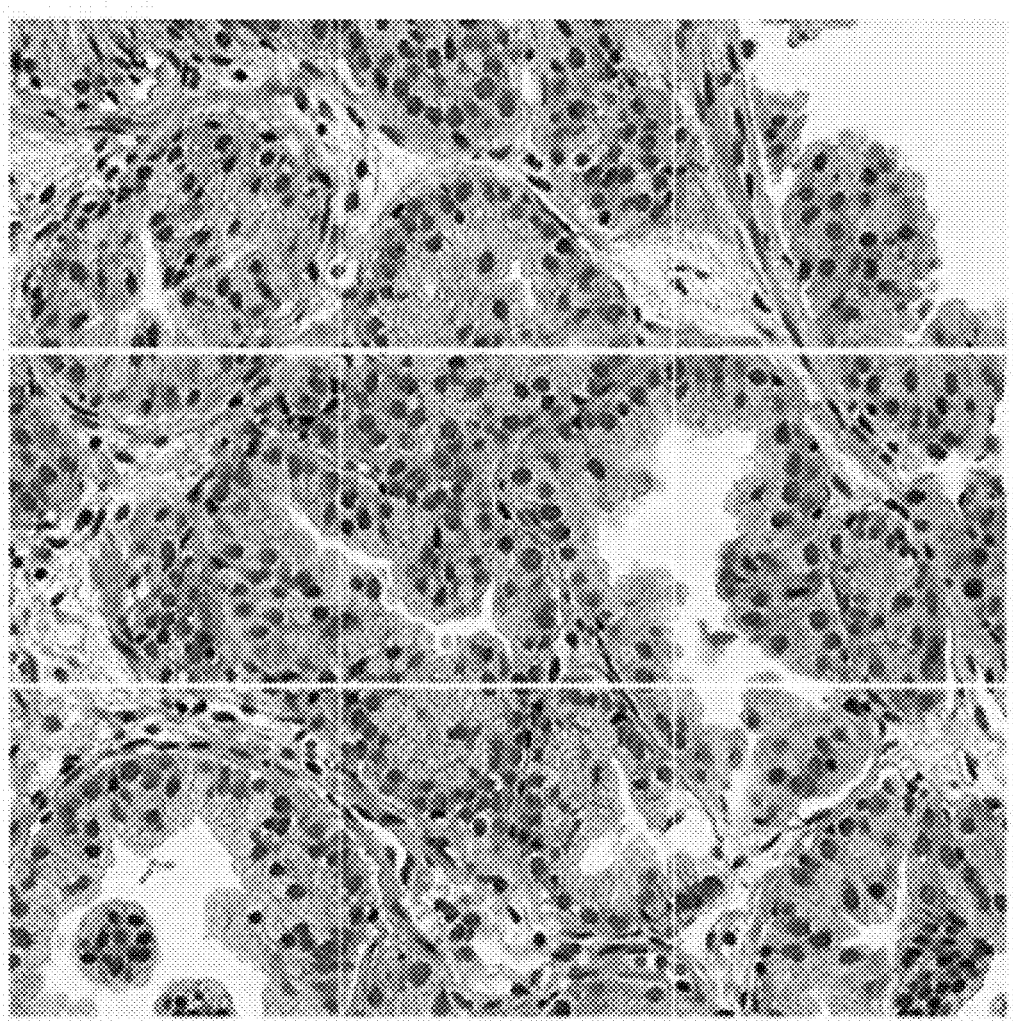
FIG. 11 is a view exemplarily illustrating a result of a diagnosis using a neural network according to an exemplary embodiment.

FIG. 11 is a view exemplarily illustrating a result of a diagnosis using a neural network according to an exemplary embodiment.

Referring to FIG. 11, a diagnosis system 100 using a neural network 200 according to an exemplary embodiment may output a diagnosis result of the tile at the center among the tiles, as shown in the lower portion of the image shown in FIG. 11.

For example, the diagnosis system 100 has determined that the value of a first correlation factor channel is 0.90, the value of a second correlation factor channel is 0.73, the value of a third correlation factor channel is 0.95, the value of a fourth correlation factor channel is 0, the value of a first state channel is 0.64, the value of a second state channel is 0.4, and the value of a third state channel is 0, for the tile at the center among the tiles shown in FIG. 11 using the trained neural network 200.

As such, the tile at the center may be determined to be highly probable that the Gleason pattern is 3, the cell nucleus satisfies a specific condition, the tile corresponds to a single cell layer, and the tile corresponds to a high density gland.

Figure 12:
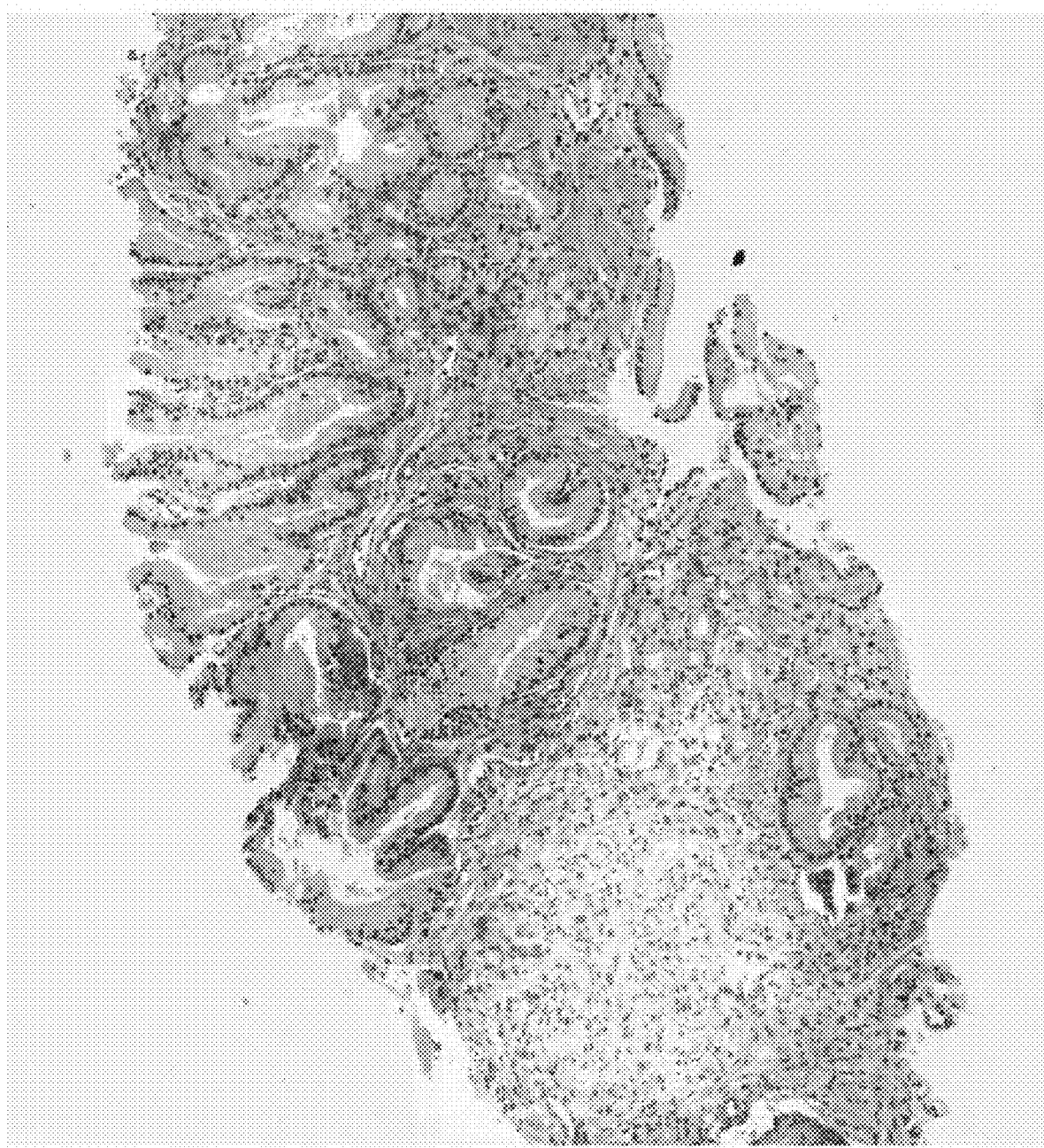
FIG. 12 is a view illustrating a biometric image diagnosed through a disease diagnosis system using a neural network according to an exemplary embodiment.

FIG. 12 is a view illustrating a biometric image diagnosed through a disease diagnosis system using a neural network according to an exemplary embodiment.

FIG. 12 exemplarily shows a result, in which the parts thereof where prostate cancer has developed in a biometric image are shown differently according to a degree of progression through the diagnosis system 100 according to an exemplary embodiment. FIG. 12 shows that the part expressed in green color is a biological tissue corresponding to Gleason pattern of 3, the part expressed in violet color is a biological tissue corresponding to Gleason pattern of 4, and the part expressed in red color is a biological tissue corresponding to Gleason pattern of 5.

Accordingly, the diagnosis system 100 according to an exemplary embodiment may automatically and effectively diagnose a disease within a short amount of time as compared to when conducted by trained pathology workers. In addition, as a state channel is defined to be included in a plurality of output layers according to a degree of progression of a disease, the varying difference of the degree of progression of a disease in a biological tissue may be visualized in a diagnosis result as shown in FIG. 12.

In addition, it has been confirmed that diagnosing a single tile with reference to both the single tile and a macro-tile including the single tile improves the accuracy of diagnosis as compared with a case of simply training only a single tile as described above.

In addition, although the diagnosis system according to an exemplary embodiment has been mainly described above with reference to diagnosing prostate cancer, the inventive concepts are not limited thereto, and may be applied for diagnosing other types of diseases, which may perform a diagnosis on a specific tissue considering the states of tissues around the corresponding tissue, as well as the state of the specific tissue.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

The invention claimed is:

1. A disease diagnosis system implemented in a system including a processor and a storage device for storing a neural network and using a biometric image and the neural network, the disease diagnosis system comprising:
   a micro-neural network for receiving a first tile included in the biometric image through a first input layer, the micro-neural network including a plurality of first layers and an output layer; and
   a macro-neural network for receiving a macro-tile including the first tile and at least one or more second tiles adjacent to the first tile through a second input layer, the macro-neural network including a plurality of second layers and the output layer,
   wherein the output layer includes at least one state channel indicating a state of a disease of a biological tissue corresponding to the first tile.

2. The system according to claim 1, wherein the output layer is determined on the basis of output data of a first right-before layer included in the first layers and located closest to the output layer, and a second right-before layer included in the second layers and located closest to the output layer.

3. The system according to claim 1, wherein the macro-neural network has a larger stride than the micro-neural network.

4. The system according to claim 1, wherein the output layer includes:
   the state channel; and
   at least one correlation factor channel indicating a degree of manifestation of a correlation factor associated with a value of the state channel.

5. The system according to claim 4, wherein the disease is prostate cancer.

6. The system according to claim 5, wherein the state channel indicates a probability of a biomedical tissue corresponding to the first tile to have a Gleason pattern value of a predetermined range.

7. The system according to claim 5, wherein the correlation factor channel includes:
   a first channel indicating a probability that a cell nucleus of the biological tissue corresponding to the first tile satisfies a predetermined condition;
   a second channel indicating a probability that the biological tissue corresponding to the first tile is classified as a single cell layer;
   a third channel indicating a probability that the biological tissue corresponding to the first tile is classified as a high density gland; and
   a fourth channel indicating a probability that the biological tissue corresponding to the first tile is classified as normal stroma.

8. A method of diagnosing a disease using a neural network, performed by a disease diagnosis system implemented in a system including a processor and a storage device and using a biometric image and the neural network, the method comprising the steps of:
   storing a micro-neural network for receiving a first tile included in the biometric image through a first input layer, the micro-neural network including a plurality of first layers and an output layer, and a macro-neural network for receiving a macro-tile including the first tile and at least one or more second tiles adjacent to the first tile through a second input layer, the macro-neural network including a plurality of second layers and the output layer; and
   training the micro-neural network and the macro-neural network using annotation information annotated in the first tile to correspond to the output layer,
   wherein the output layer includes at least one state channel indicating a state of a disease of a biological tissue corresponding to the first tile.

9. The method according to claim 8, further comprising the steps of:
   receiving a target tile included in a diagnosis target biometric image, by the neural network including the trained micro-neural network and macro-neural network; and
   outputting an output data corresponding to the output layer through the neural network.

10. The method according to claim 8, wherein the output layer is determined on the basis of output data of a first right-before layer included in the first layers and located closest to the output layer, and a second right-before layer included in the second layers and located closest to the output layer.

11. The method according to claim 8, wherein the macro-neural network has a larger stride than the micro-neural network.

12. The method according to claim 8, wherein the output layer includes:
   the state channel; and
   at least one correlation factor channel indicating a degree of manifestation of a correlation factor associated with a value of the state channel.

13. A computer program installed in a data processing device and recorded in a medium to perform the method of claim 8.

14. A method of diagnosing a disease using a neural network, performed by a disease diagnosis system implemented in a system including a processor and a storage device for storing the neural network and using a biometric image and the neural network, the method comprising the steps of:
   storing the neural network including a first input layer for receiving a first tile included in the biometric image, a plurality of layers, and an output layer; and
   training the neural network using the first tile and annotation information of the first tile corresponding the output layer, wherein the output layer includes at least one state channel indicating a state of a disease of a biological tissue corresponding to the first tile, and at least one correlation factor channel indicating a degree of manifestation of a correlation factor associated with a value of the state channel.

15. A computer program installed in a data processing device and recorded in a medium to perform the method of claim 14.

* * * * *